(12) United States Patent
Von Schuckmann

(10) Patent No.: US 9,579,473 B2
(45) Date of Patent: Feb. 28, 2017

(54) DEVICE FOR INHALING PULVERULENT SUBSTANCES

(76) Inventor: Alfred Von Schuckmann, Kevelaer (DE)

( * ) Notice: Subject to any disclaimer, the term of this patent is extended or adjusted under 35 U.S.C. 154(b) by 267 days.

(21) Appl. No.: 14/114,986

(22) PCT Filed: May 12, 2011

(86) PCT No.: PCT/EP2011/057686
§ 371 (c)(1),
(2), (4) Date: Oct. 31, 2013

(87) PCT Pub. No.: WO2012/152333
PCT Pub. Date: Nov. 15, 2012

(65) Prior Publication Data
US 2014/0076315 A1 Mar. 20, 2014

(51) Int. Cl.
*A61M 16/00* (2006.01)
*A61M 15/00* (2006.01)

(52) U.S. Cl.
CPC ...... *A61M 15/0028* (2013.01); *A61M 15/003* (2014.02); *A61M 15/0026* (2014.02); *A61M 15/0035* (2014.02); *A61M 15/0041* (2014.02); *A61M 15/0063* (2014.02); *A61M 2202/064* (2013.01); *A61M 2206/14* (2013.01); *A61M 2206/16* (2013.01)

(58) Field of Classification Search
CPC ........ A61M 15/0028; A61M 2202/064; A61M 15/0026; A61M 15/003; A61M 15/0035; A61M 2206/16; A61M 15/0041; A61M 15/0021; A61M 15/0025; A61M 15/00; A61M 16/00

USPC ............. 128/203.15, 203.21, 205.21, 206.21
See application file for complete search history.

(56) References Cited

U.S. PATENT DOCUMENTS

| 5,048,514 A | 9/1991 | Ramella |
| 5,685,294 A * | 11/1997 | Gupte ............... A61M 15/0028 128/203.15 |
| 2011/0120465 A1 | 5/2011 | Haerder et al. |

FOREIGN PATENT DOCUMENTS

| CA | 2 379 137 A1 | 2/2001 |
| CA | 2 642 084 A1 | 2/2001 |
| CA | 2 509 521 A1 | 6/2004 |
| DE | 690 04 749 T2 | 6/1994 |
| DE | 10 2008 014025 A1 | 9/2009 |
| EP | 1 923 087 A2 | 5/2008 |
| WO | 2004/052435 A1 | 6/2004 |
| WO | 2007/144659 A1 | 12/2007 |
| WO | WO 2008065403 A2 * | 6/2008 ........ A61M 15/0028 |

OTHER PUBLICATIONS

International Search Report of PCT/EP2011/057686, mailed Feb. 1, 2012.

* cited by examiner

*Primary Examiner* — Bradley Philips
*Assistant Examiner* — Victoria Leszczak
(74) *Attorney, Agent, or Firm* — Collard & Roe, P.C.

(57) ABSTRACT

A device, which is closable by a cap, for inhaling powdery substances, particularly of a medicinal kind, contained in capsules is displaced by a slider into an emptying position for the purpose of aspirating completely the content thereof. The air inlet for the mouthpiece channel is adjacent to and below the closed mouthpiece cap.

2 Claims, 11 Drawing Sheets

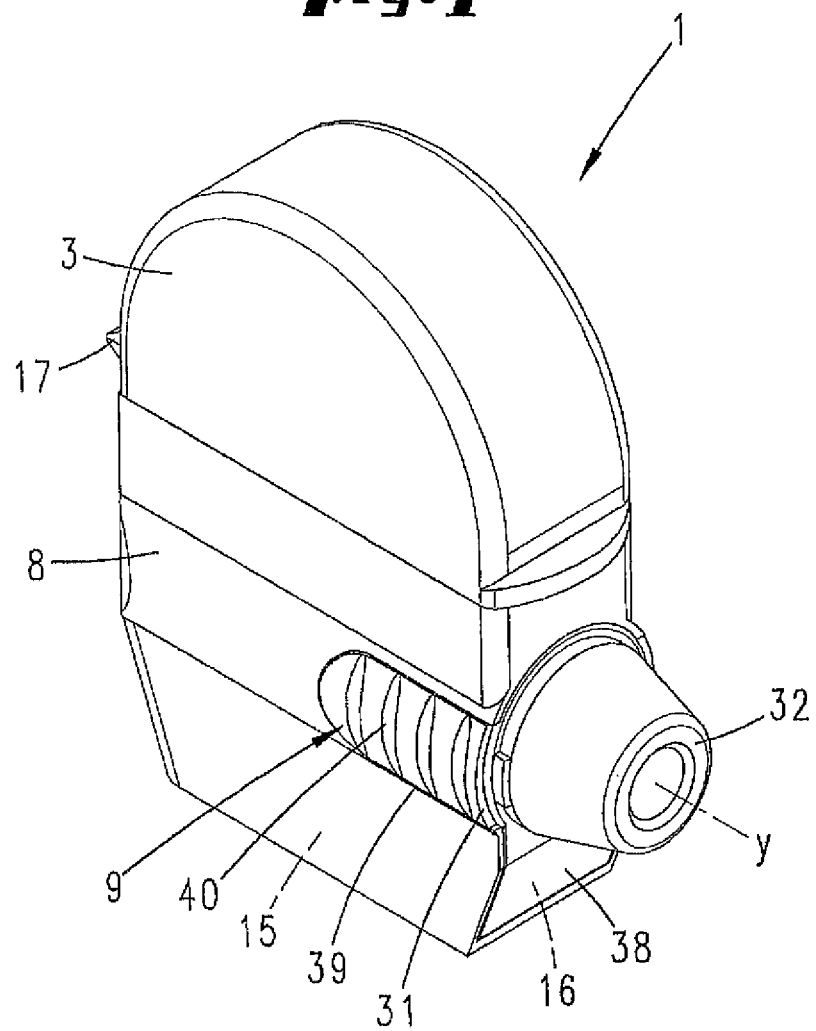

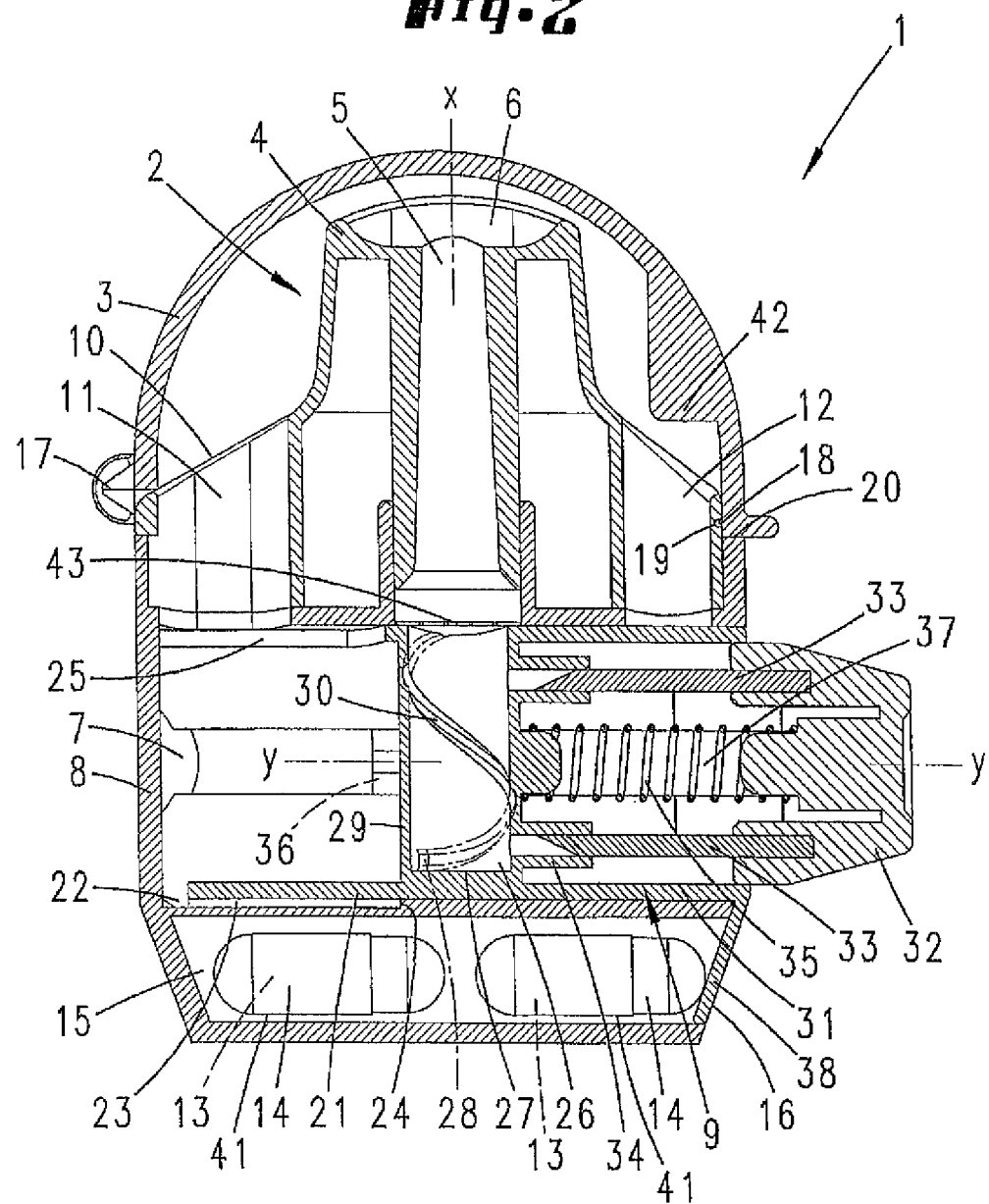

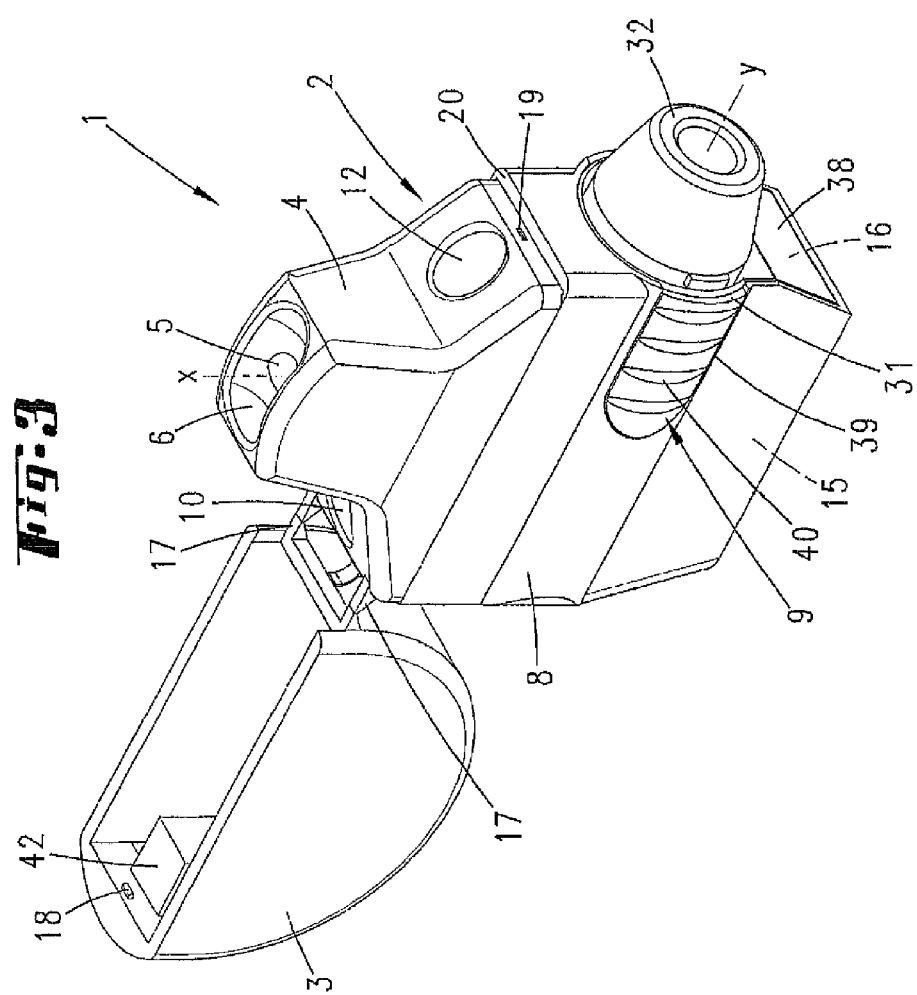

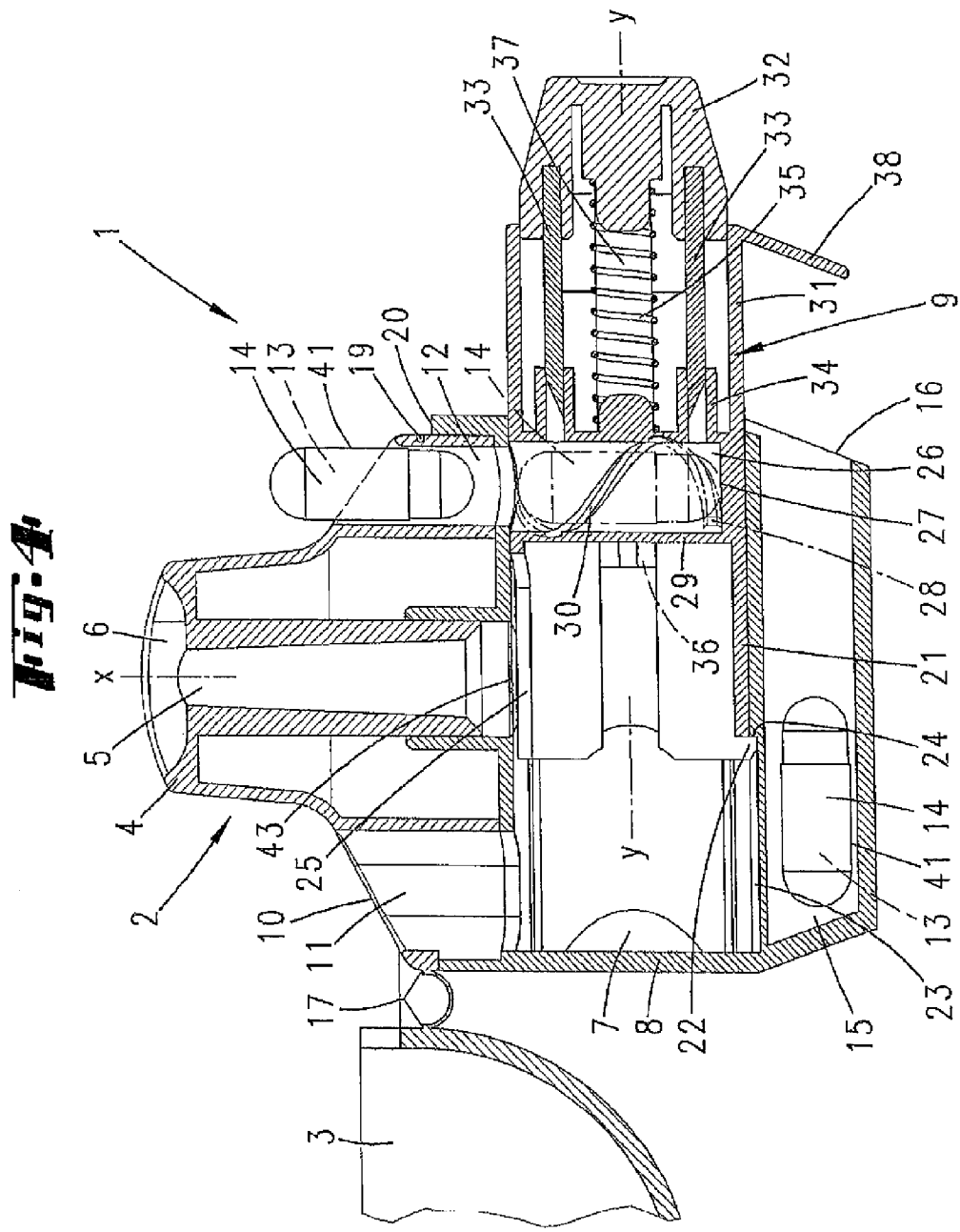

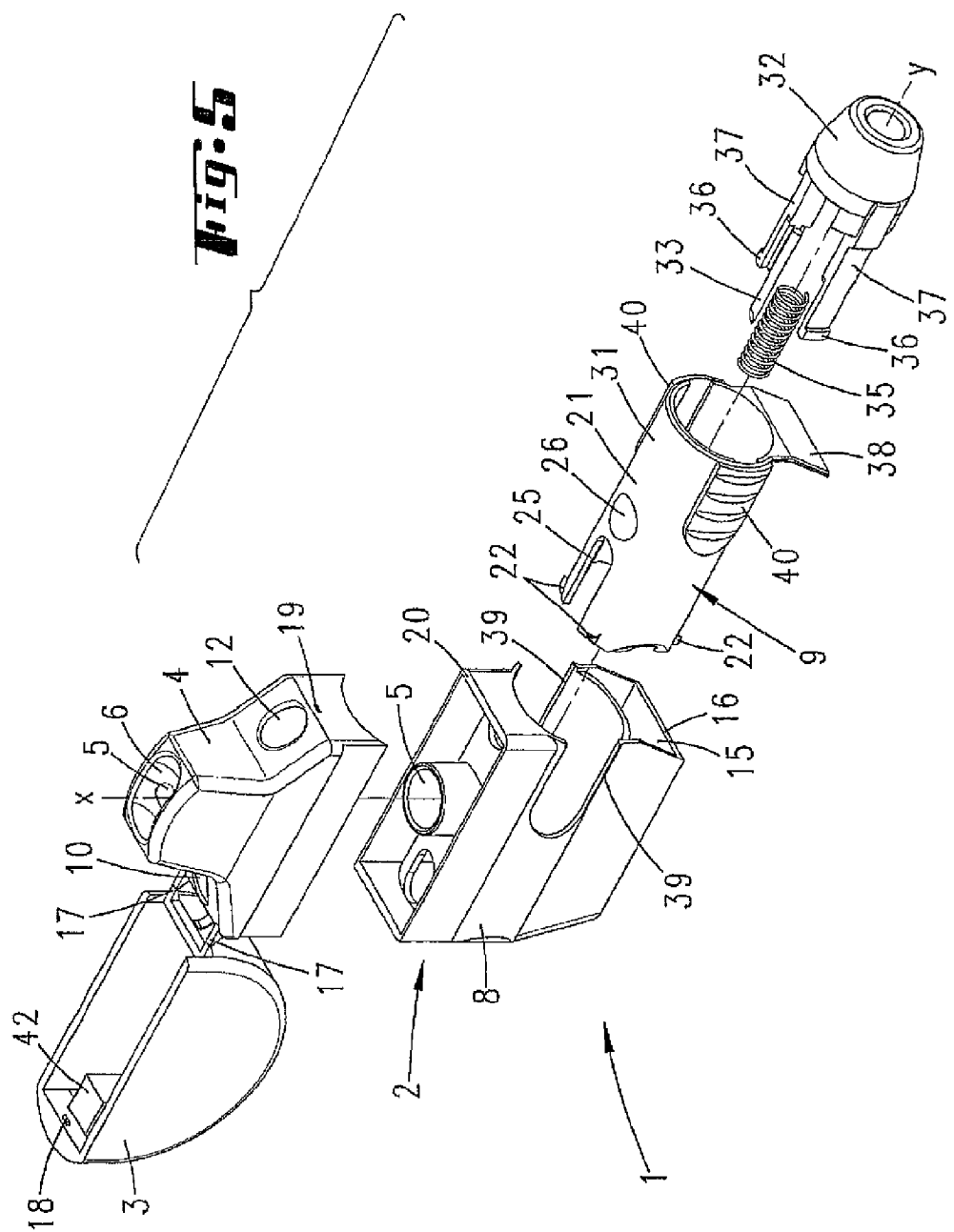

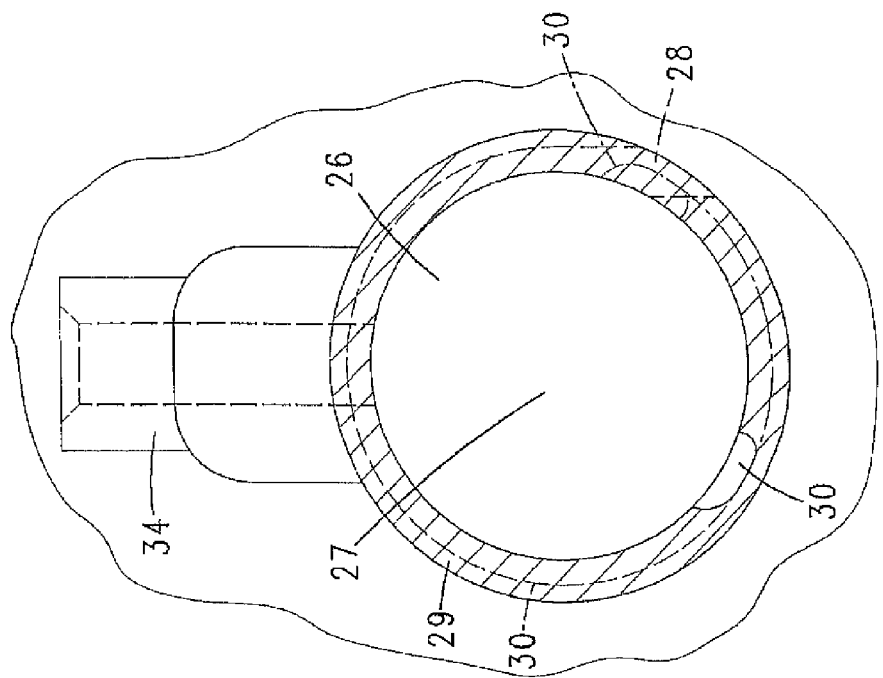
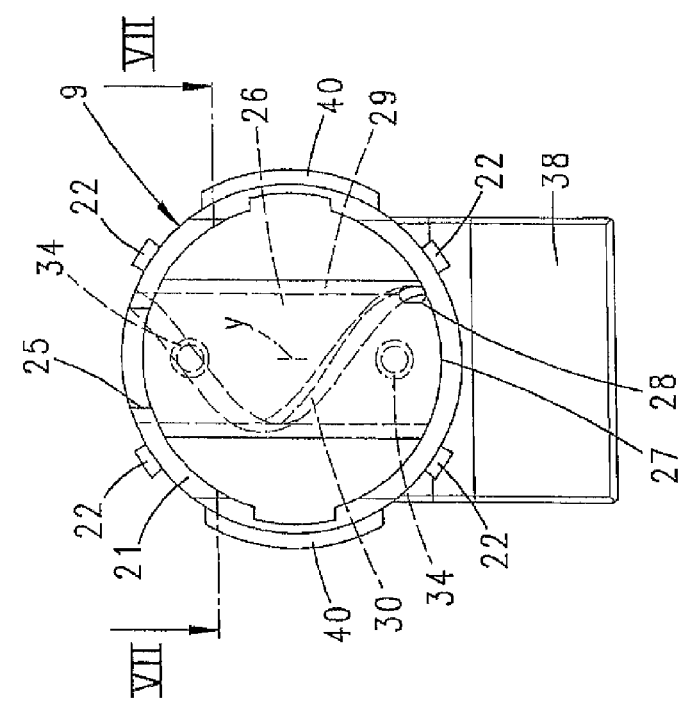

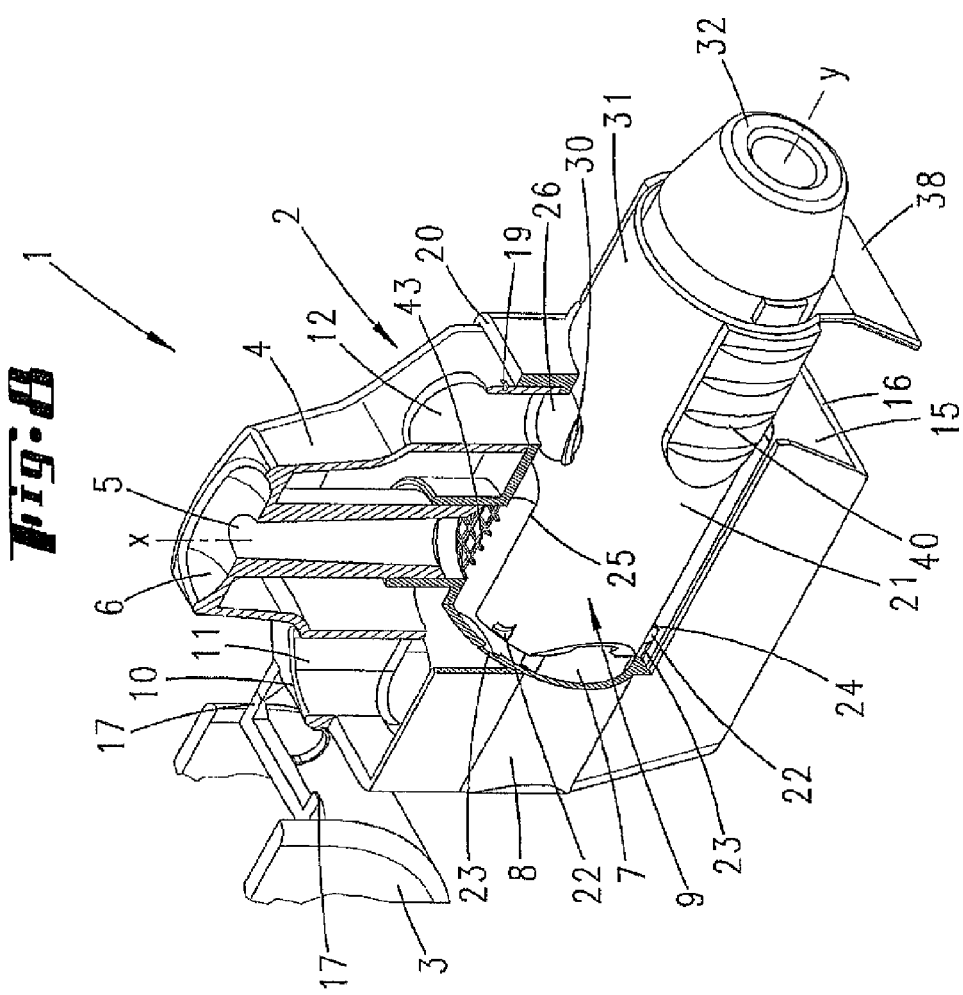

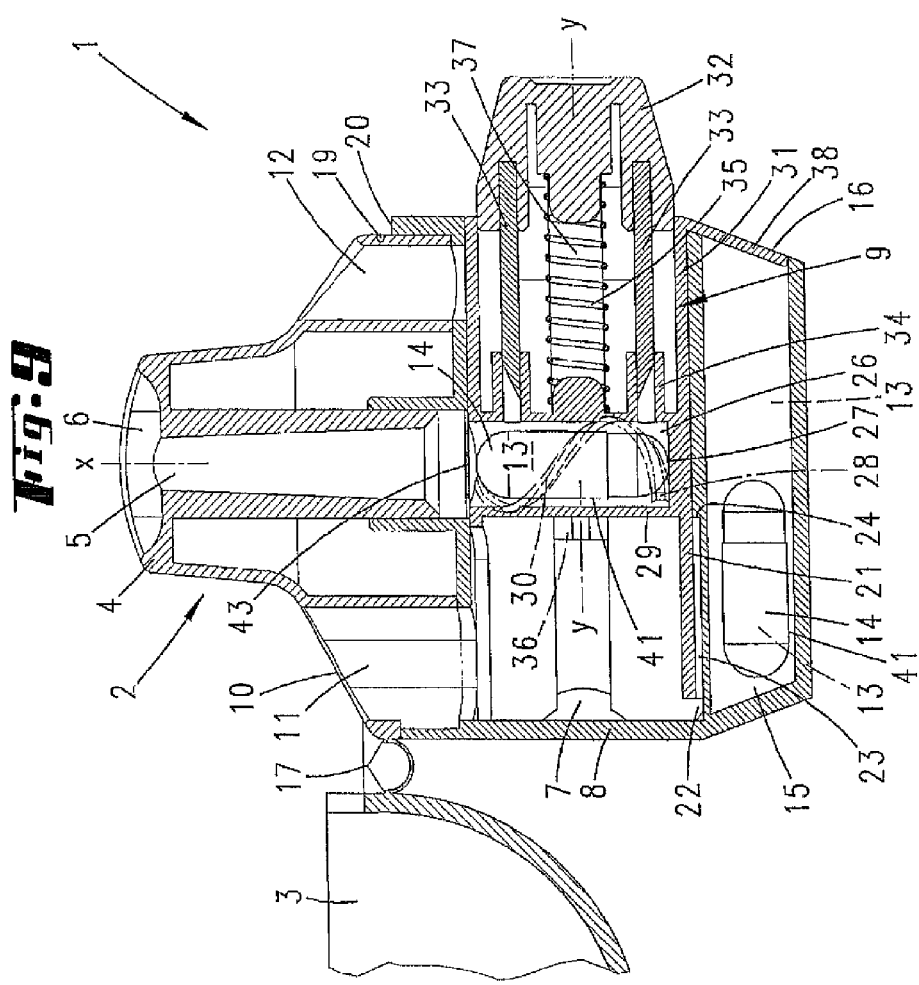

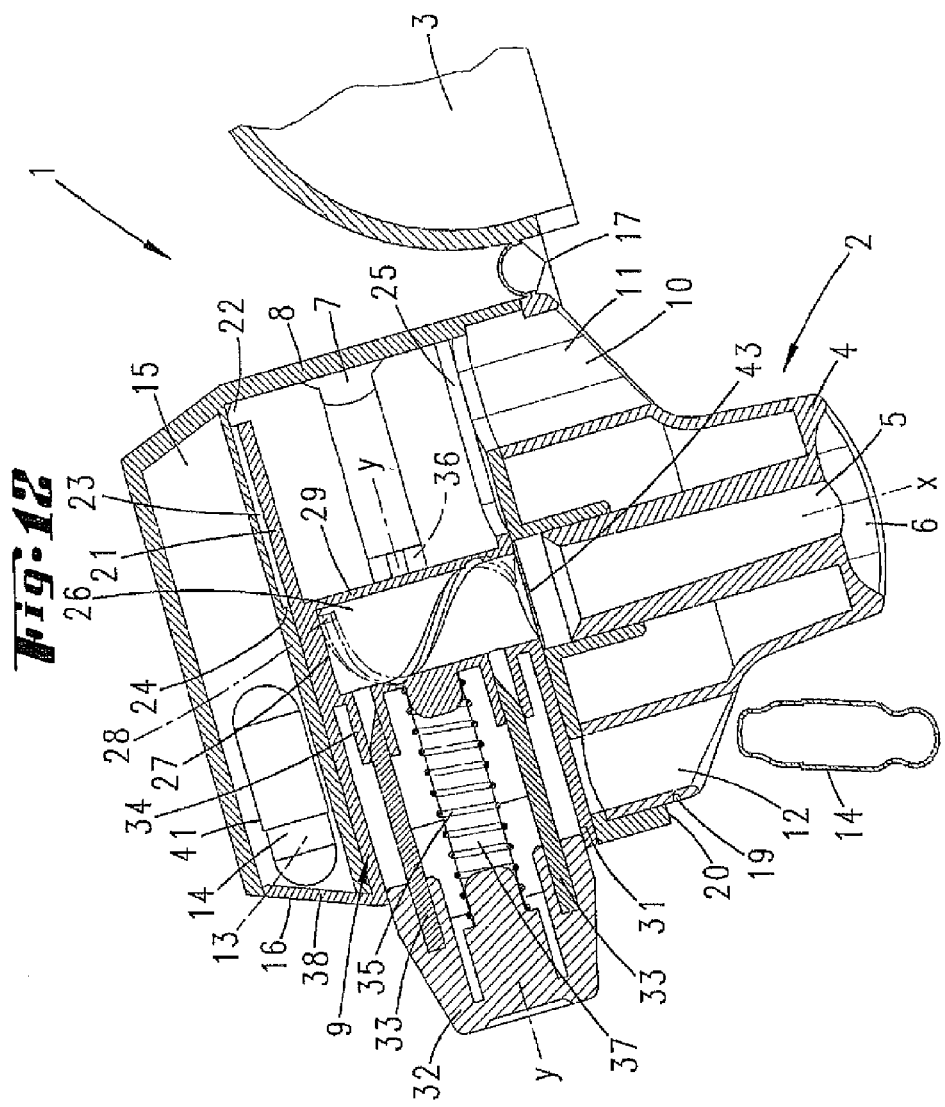

DEVICE FOR INHALING PULVERULENT SUBSTANCES

CROSS REFERENCE TO RELATED APPLICATIONS

This application is the National Stage of PCT/EP2011/057686 filed on May 12, 2011, the disclosure of which is incorporated by reference. The international application under PCT article 21(2) was not published in English.

The invention relates to a device for inhaling powdery substances, particularly of a medicinal kind, from capsules that are displaceable by means of a slider into an emptying position, in which position the capsule wall can be pierced, by means of displaceable needles, for aspirating completely the content of the capsule through a mouthpiece channel, which runs in axial extension of the capsule chamber and is overlaid by a hinged-on cap in the manner of a cover.

Devices of the kind in question are known (DE 10 2008 014 025 A1). As a result of aspiration through the mouthpiece, and accordingly also through the capsule chamber, the powdery substance is emptied out of the capsule through the openings that were pierced through the capsule wall, and then inhaled by way of the aspirated air flow. The entry of the aspirated air is effected through one or more openings on the underside of the capsule chamber. These solutions are very vulnerable to contamination, because these devices are frequently left lying freely around or are even carried in the pocket. This is particularly problematic when such contamination gets into the interior, which is in practice not accessible to the user without doing damage.

In view of the previously described prior art, it is a technical object of the present invention to improve a device of the kind in question, in particular with regard to a discharge of the substance from the capsule which is always the same.

This object is achieved substantially by the subject matter according to the invention. When not in use, the air entry opening is closed off by a cover. During use, it is practically impossible for the gripping hand to close off the air entry. It has also been found that no problems are caused if the lips of the aspirating mouth reach almost as far as the edge of the inlet opening. This latter in fact controls the aspiration operation. The air inlet is also practically at the farthest spacing from the inlet opening of the capsule chamber, so that a longer air path for uniformity of flow is achieved as far as possible. In the closed position of the cap, both the air inlet point and also the aspiration point are always protected against contamination. Preferably, this protective function can also be achieved when the cap is closed, in that a capsule insertion channel is located radial oppositely from the air inlet opening, so that this channel also is covered by the hinged cap in the closed position.

The invention is described in further detail below based on the appended drawings, which illustrate only a single embodiment.

FIG. 1 shows the device in a perspective view, in a non-use position, with a lid closing the device;

FIG. 2 shows the device according to FIG. 1 in vertical longitudinal section;

FIG. 3 is an illustration corresponding to FIG. 1, but in a position preparatory to use;

FIG. 4 shows the longitudinal section thereof;

FIG. 5 shows an exploded perspective view of the device;

FIG. 6 shows a detail illustration of the front view, looking onto a slider of the device;

FIG. 7 shows the enlarged sectional view along the line VII-VII in FIG. 6, through a capsule chamber in the slider;

FIG. 8 shows a perspective view of the device corresponding to FIG. 3, but partially cut away;

FIG. 9 shows a sectional view corresponding to FIG. 4 for the position of displacement of the slider into the inhaling position thereof;

FIG. 12 shows a further longitudinal sectional view through the device for a position in the course of the discarding of the capsule after inhalation has been completed.

Figure 10:
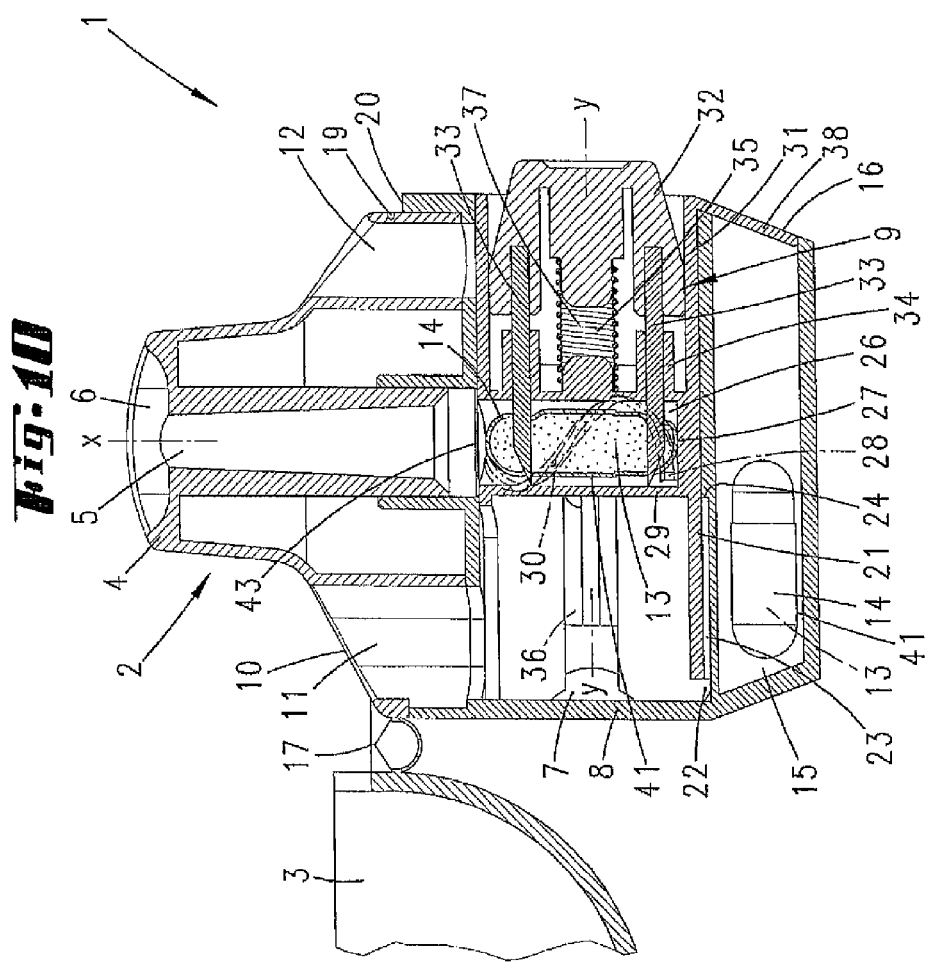
FIG. 10 shows a subsequent view following FIG. 9, in the course of piercing a capsule that is accommodated inside the capsule chamber in the slider.
Figure 11:
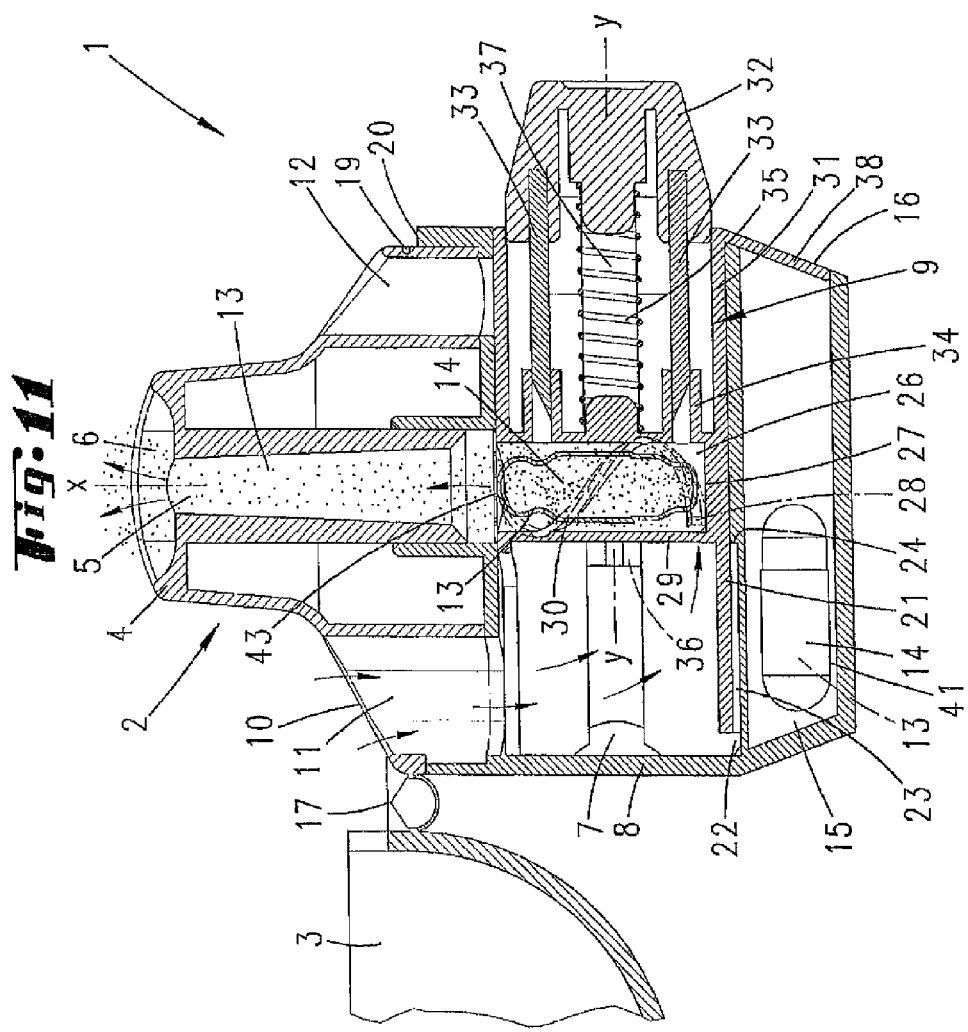
FIG. 11 shows a subsequent view following FIG. 10, for the inhalation process.

Illustrated and described are, in first instance with regard to FIG. 1, a device 1 for inhaling powdery substances in the manner of a capsule inhaler, the device 1 being implemented as a convenient portable pocket unit. The device has a housing 2 to which a cover-like cap 3 is hinged. In the closed position of the cap, further corresponding to a position of non-use according to FIGS. 1 and 2, the device 1 has a length-to-height ratio of approximately 1:1 to 1:1.5, as well as a depth that is perpendicular to the height extent, i.e., a depth that is perpendicular to the image plane viewed in FIG. 2, that is approximately ⅕ of the height extent of the housing 2 when closed by the cap. The components of the device 1 are preferably made of plastics injection-molded parts.

The housing 2 in first instance forms a mouthpiece 4 which, viewed in the direction of width of the housing 2, is centrally disposed and elevated in the direction of height of the housing 2 relative to the adjacent housing portions on both sides, so that the mouthpiece 4 can be comfortably surrounded by the lips.

A mouthpiece channel 5 which extends vertically, with respect to the illustrations, in the region of an outwardly open mouthpiece outlet 6, opens into the mouthpiece 4. The mouthpiece channel 5 starting from the mouthpiece outlet, 6, extends over approximately one-half the vertical height of the housing 2 and terminates in an open-ended manner at the opposite end from the mouthpiece outlet 6 in a slide chamber 7 formed in the housing 2. The slide chamber extends perpendicularly with respect to the mouthpiece channel 5, accordingly in the direction of width of the housing 2, as a whole continuing approximately over the entire width of the housing 2.

At one end at the front, the slide chamber 7 is closed by the housing wall 8, which also encloses the slide chamber 7 peripherally. At the other end, the slide chamber 7 passes through the associated housing wall in order to receive a slider 9 which is to be actuated, and is accordingly accessible, from the outside.

Associated with the slide chamber end which is closed by means of the housing wall 8, the housing 2 includes an air inlet opening 10. This opening, viewed in the direction of width of the housing 2, is positioned adjacently and axially offset by approximately one-half the axial extent of the mouthpiece channel 5 relative to the mouthpiece outlet 6. The air inlet opening 10 merges into an air inlet channel 11 that extends substantially parallel to the mouthpiece channel 5 and opens into the slide chamber 7.

With respect to a central axis x which passes through the mouthpiece channel 5, an insertion channel 12 is formed on the opposite side from the air inlet opening 10 and the air inlet channel 11, is adjacent to the mouthpiece 4 and the mouthpiece channel 5, is also aligned parallel to the mouthpiece channel 5 and to the axis x, and exits in an open-ended manner to the outside, passing through the housing wall in the same manner as the air inlet opening 10. At the other end, the insertion channel 12 opens into the slide chamber 7.

The same as for the mouthpiece channel 5 as well as the air inlet channel 11, the insertion channel 12 has a circular cross-section, the diameter of the insertion channel 12 being adapted to the diameter of a capsule 14 which is to be inserted through this channel and contains the powdery substance 13 to be inhaled. It is further preferred that the diameter of the insertion channel 12 is provided with an excess dimension relative to the diameter of the capsule 14, more preferably, with a diameter that is sized such that is corresponds to 1.1 to 1.3 times the diameter of the capsule, so that the capsule 14 is able to slip without much friction through the insertion channel 12 when handled appropriately. During insertion, the capsule 14 falls more or less freely, through the insertion channel 12 and into a capsule chamber, as described in further detail below.

The slide chamber 7 is also supported from below by a housing portion which forms a storage space 15 for capsules 14. Except for a removal opening 16 which faces in the same direction as the opening of the slide chamber 7, the storage space is enclosed on all sides by the housing wall 8. A daily ration of capsules 14, for example, may be carried along in the storage space 15.

In the narrow-side region adjacent to the air inlet opening 10, the cap 3, which on the outside of the housing wall has substantially the shape of a half-shell, is connected to the housing 2, preferably in one piece and more preferably integrated into the material, by means of a hinge 17. The hinge 17 is a so-called snap-action hinge having a clasp action, and is also preferably designed in such a way that the pivot position of the cap 3 is self-locking in the open position, which opens up the mouthpiece 4 as well as the air inlet opening 10 and the insertion channel 12. In the closed position of the cap according to FIGS. 1 and 2, the cap 3 overlies the air inlet opening 10 and the insertion channel 12 as well as the mouthpiece 4, the closed position of the cap also being locked. A detent catch 18 which is molded onto the interior side of the cap on the interior wall of the cap opposite from the hinge 17, and which engages in a detent recess 19 which is formed in the outer side of the wall of the insertion channel 12, serves for this purpose. In the closed position, the portion of the cap facing the detent catch 18 is further supported on a step 20 of the housing wall 8.

The slide chamber 7 has a substantially hollow cylindrical shape. The mentioned slider 9 is displaceably disposed in the longitudinal extent of the slide chamber 7, and thus transversely relative to the axis x, for which purpose the slider 9 further has an outside diameter that is adapted to the inside diameter of the slide chamber 7. Accordingly, the slider wall 21 is configured for contact with the periphery of the wall of the slide chamber 7.

In the region of the end of the slider 9 that engages into the slide chamber 7, the slider is provided with a plurality of radial protrusions 22 (in the illustrated exemplary embodiment, four) which are evenly distributed around the circumference. The protrusions engage into correspondingly formed and positioned grooves 23, parallel to the slider axis y, which are formed in the wall of the slide chamber 7 and which, starting from the closed front wall of the slide chamber 7, extend to a location approximately level with the opening of the mouthpiece channel 5, thus forming stop shoulders 24 for the radial protrusions 22 in this region at the end of the grooves 23. These stop shoulders limit the displacement movement of the slider 9 radially outwardly with regard to the axis x.

Particularly for the fitting of the slider 9 into the slide chamber 7, also for the routing of the air during the inhalation process, the end portion of the slider 9, which carries the radial protrusions 22, is longitudinally slotted, resulting in windows 25 in the slider wall 21, parallel to the slider axis y, which terminate in an open-ended manner toward the free end of the slider 9.

The slider 9 also has a capsule chamber 26. The capsule chamber is disposed, with regard to the free end of the slider 9, to the rear of the slotted slider wall portion and extends transversely relative to the slider axis y, further in parallel alignment with the axis x of the mouthpiece channel 5, more preferably with a hollow cylindrical configuration of the chamber. The capsule chamber 26 is substantially circumferentially closed by the slider wall 21, while at the same time the slider wall 21 also forms a closed base 27 of the capsule chamber 26. The end of the capsule chamber 26 opposite from the base is radially outwardly open with respect to the slider axis y, thus in particular for the entry of a capsule 14 into the capsule chamber 26. In the illustrated exemplary embodiment, the diameter of the capsule chamber 26 is selected in such a way that its diameter corresponds approximately to 1.2 to 1.4 times the diameter of the capsule, so that a capsule 14 which is inserted into the capsule chamber 26 rests loosely in a standing position on the base 27.

An access opening 28 for the air to be aspirated is formed in the region of the bottom end of the capsule chamber 26. This access opening is also configured such that the air entering through same enters into the space of the capsule chamber substantially tangentially. The access opening 28 opens on the exterior side into the slide chamber 7 or the cavity of the slider 9 which is partially enclosed by the slider wall 21 and which opens into the slide chamber 7. On the inside of the chamber, the access opening 28 opens into a thread 30 that is formed in the chamber wall 29. In the illustrated exemplary embodiment, the thread 30 is formed as a substantially S-shaped groove which, starting from the bottom end of the capsule chamber 26 and extending to the top end of the capsule chamber 26, accordingly extends upwardly along the chamber wall 29 in the direction of the open end of the capsule chamber 26. The thread 30 runs around the chamber wall 29 and over the entire axial height extent thereof over a circumference of approximately 360°. The arrangement is further selected such that the associated access opening 28 represents, in a manner of speaking, an extension of the groove-like thread 30 that passes through the chamber wall 29.

After the capsule chamber 26, the slider 9 continues radially outwardly in the form of a slider sleeve 31. A push button-like actuating handle 32 is mounted in the slider sleeve to be displaceable in the direction of extent of the slider axis y. In a starting position for the actuation, the actuating handle 32 extends freely beyond the outwardly facing end of the slider sleeve 31. Disposed axially on the inside are two needles 33, which are secured to the actuation handle 32 and extend parallel to the slider axis y with equidistant spacing from this axis, and are disposed one above the other with regard to a vertical projection onto a base plane of the housing 2. At their ends, these needles 33 are guided inside guide bushings 34 that are formed from the slider wall 21, and whose guide channels pass through the chamber wall 29 and open freely into the capsule chamber 26.

The actuation handle 32 is supported via a compression spring 35, which is concentrically disposed relative to the slider axis y, against the region of the chamber wall 29 facing the inside of the slider sleeve 31, in such a manner that the compression spring 35 places an axially outward load on the actuation handle 32 with regard to the slider axis y. A stop limit for the actuation handle 32 in this regard is achieved due to the arrangement of radial protrusions 36 on spring arms 37 which are molded onto the actuation handle 32 and extend parallel to the slider axis y. The radial protrusions 36 interact with stop shoulders of the slider sleeve 31, not shown in further detail in the illustrations.

The spring force of the compression spring 35 is selected such that it is less than the slider displacement force of the slider 9 in the slide chamber 7, and accordingly is selected to be less than the frictional force between the slider wall 21 and the housing wall 8 that delimits the slide chamber 7.

With reference to the illustrations, on the bottom side of the slider sleeve 31, in the region of the edge that delimits the opening for the actuation handle 32 to pass through, a vertically downwardly facing closure wall 38 is molded on for closing the removal opening 16 when the device 1 is in the non-use position, i.e., in the inwardly displaced position of the slider 9 into the slide chamber 7.

To carry out an inhalation process, first the cap 3 is pivoted open around the hinge 17, and about a hinge axis that is oriented transversely relative to the axis x and in the depth direction of the housing 2, in order to expose the mouthpiece 4 and the air inlet opening 10 as well as the insertion channel 12. In this starting position, the slider 9 is retracted and is disposed inside the slide chamber 7, this retracted position being stop-limited by a stop of the slider wall portion, which has the radial protrusions 22, against the housing wall 8 which closes the slide chamber 7 at the front. In this stop-limited position, the capsule chamber 26 is disposed in an axial extension of the mouthpiece channel 5. The slider sleeve 31 of the slider 9 is retracted to such an extent that its outwardly facing free circumferential rim edge is disposed in the plane of the housing wall portion which is passed through. Due to its spring-loaded basic position, the actuation handle 32 extends correspondingly, beyond the associated narrow-side wall of the housing 2.

The slider wall 21 is partially exposed in the region of the slider sleeve 31 for gripping by the user, for which purpose window-like recesses 39 are provided in the surfaces on the wide sides of the housing 2. These recesses have a slot-like configuration with open ends toward the end wall of the housing 2, through which the actuation handle 32 passes. Grip portions 40 which are mounted on the slider sleeve 31 on the outside of the wall extend through these recesses 39.

As the result of grasping the grip portions 40 by the fingers of one hand while simultaneously grasping the housing 2 with the other hand, the slider 9 is initially pulled out to the stop limit. In this stop-limited pulled-out position, the capsule chamber 26 is disposed in axial prolongation of the insertion channel 12, so that a capsule 14 is insertable into the capsule chamber 26 via the insertion channel 12. The capsule 14 can already have been inserted into the insertion channel 12 prior to a corresponding displacement of the slider 9, whereby, after the corresponding displacement of the slider 9, the capsule 14 automatically drops into the capsule chamber 26. Alternatively, the storage space 15 is exposed in the extended position of the slider for the removal of a new capsule 14, which can be subsequently inserted via the insertion channel 12.

As the result of returning the slider 9 into its inserted and stop-limited position in the slide chamber 7 according to FIG. 9, the capsule 14, which is accommodated in the capsule chamber 26, is moved in axial association with the mouthpiece channel 5. The displacement of the slider 9 preferably occurs as the result of pressing on the actuation handle 32, whereby the compression spring 35 which acts upon the actuation handle 32 does not permit a relative movement between the actuation handle 32 and the slider 9 to occur in the course of the slider displacement.

In the stop-limited slider insertion position, the restoring force of the compression spring 35 is preferably overcome due to a further pressure load on the actuation handle 32, resulting in a corresponding relative movement of the actuation handle 32 with respect to the slider 9, which is stationary due to the action of the stop limit, corresponding to a relative displacement of the needles 33 which are fixed on the actuation handle 32. The tips of the needles pass through the guide bushings 34 into the capsule chamber 26, piercing the capsule wall 41 in the further course of the displacement, when the needle tips pass into the interior of the capsule as well as when they emerge from the capsule interior toward the outside. The arrangement of the needles 33 is selected such that they pierce the capsule 14 in each case in the region of the transition from the cylindrical center portion to the cap end portions. After relieving the pressure load on the actuation handle 32, due to the action via the compression spring 35, the actuation handle is automatically moved back into the stop-limited basic position in which the needles 33 are once again pulled out of the region of the capsule chamber 26.

In the associated position of the capsule chamber 26 in the axial extension of the mouthpiece channel 5, the insertion channel 12 is closed on the base side by the wall of the slider sleeve 31.

For inhaling, the mouthpiece 4 is enclosed by the lips, after which an air flow is generated due to inhaling. The air flow enters the air inlet channel 11 via the air inlet opening 10 and into the cavity of the slider 9 that is formed by the slotted slider wall 21, and is aspirated through the access opening 28 into the capsule chamber 26, where, inside the capsule chamber 26 and the following mouthpiece channel 5, there impinges, on the air flow passing through axially, in addition a movement in the peripheral direction, due to the thread-like configuration of the capsule chamber wall 29, such that the air flow passes through the capsule chamber 26 in a turbulent manner. While passing through, the air simultaneously flows through the pierced capsule 14 to remove the substance 13 stored there, and due to the turbulence, the substance 13 is well mixed in with the air flow. The air-substance mixture is inhaled via the mouthpiece outlet 6, the turbulent air flow being directed through the mouthpiece channel 5 to the mouthpiece outlet 6, substantially perpendicularly relative to the displacement direction of the slider 9.

In the course of the turbulent passage of air through the capsule chamber 26, the capsule 14 is entrained and thereby set in rotation until a wobbling motion of the capsule 14 inside the capsule chamber 26 is achieved, and in the associated position with respect to the mouthpiece channel 5, the capsule chamber 26 is covered by a retaining grille 43 disposed at the end of the mouthpiece channel 5. The retaining grille prevents the capsule 14 from being drawn into the mouthpiece channel 5, the mesh width of the retaining grille 43 being selected to be large enough that the particle-laden air is able to pass through same without impediment.

The emptied capsule 14 can be discarded immediately after use; alternatively, after closing the housing 2 by the cap 3, the capsule is not removed until the next inhalation process, for which purpose the slider 9 is displaced axially outwardly in each case in order to bring the capsule chamber 26 into an axial extension relative to the insertion channel 12 and, by means of this insertion channel 12, the capsule 14 can be removed by tilting the housing (see FIG. 12).

Moreover, the device 1 can be prepared for the inhalation in such a way that in the non-use position, i.e., in the closed cap position according to FIGS. 1 and 2, a capsule 14 that is filled with substance 13 is disposed inside the insertion channel 12, supported on the base side by the slider sleeve 31, and the capsule 14 is captively overlaid by a cover portion 42 that is molded onto the cap 3. When the slider 9 is pulled out, the capsule 14 drops into the capsule chamber 26, after which the slider 9 is moved back to place the capsule 14 in axial extension of the mouthpiece channel 5. After the capsule 14 has been pierced, the cap 3 is pivoted open, after which the inhalation step can be carried out.

LIST OF REFERENCE CHARACTERS

1 Device
2 Housing
3 Cap
4 Mouthpiece
5 Mouthpiece channel
6 Mouthpiece outlet
7 Slide chamber
8 Housing wall
9 Slider
10 Air inlet opening
11 Air inlet channel
12 Insertion channel
13 Substance
14 Capsule
15 Storage space
16 Removal opening
17 Hinge
18 Detent catch
19 Detent recess
20 Step
21 Slider wall
22 Radial protrusion
23 Groove
24 Stop shoulder
25 Window
26 Capsule chamber
27 Base
28 Access opening
29 Chamber wall
30 Thread
31 Slider sleeve
32 Actuation handle
33 Needle
34 Guide bushing
35 Compression spring
36 Radial protrusion
37 Spring arm
38 Closure wall
39 Recess
40 Grip portion
41 Capsule wall
42 Cover portion
43 Retaining grille x axis
y slider axis

The invention claimed is:

1. A device for inhaling powdery substance from a capsule, the device comprising:
a housing comprising:
a mouthpiece having a mouthpiece channel terminating in a mouthpiece outlet, the mouthpiece being arrange in a middle portion of the housing with respect to a width direction of the housing, the mouthpiece channel having a mouthpiece channel width, a mouthpiece channel length greater than the mouthpiece channel width, and a mouthpiece channel longitudinal axis extending along the mouthpiece channel length;
a slider configured to displace the capsule into an emptying position;
displaceable needles configured to pierce the capsule when the capsule is in the emptying position and such that contents of the capsule can be completely aspirated through the mouthpiece channel and out the mouthpiece outlet;
a capsule chamber having a capsule chamber inlet opening, a capsule chamber width, a capsule chamber length greater than the capsule chamber width, and a capsule chamber longitudinal axis extending along the capsule chamber length, the capsule chamber longitudinal axis having a parallel alignment with the mouthpiece channel longitudinal axis;
an exterior housing panel disposed on a first side of the housing and extending in a planar manner in a first plane;
an air inlet opening disposed on the first side of the housing, the air inlet opening being offset laterally from the mouthpiece outlet in the width direction of the housing, being disposed offset from the mouthpiece outlet in a direction parallel to the mouthpiece channel longitudinal axis, extending to the capsule chamber inlet opening, and beginning as a hole in the exterior housing panel in the first plane of the exterior housing panel; and
an insertion channel having an insertion channel width, an insertion channel length greater than the insertion channel width, and an insertion channel longitudinal axis extending along the insertion channel length and parallel to the mouthpiece channel longitudinal axis, the insertion channel being configured to have the capsule inserted therein and to direct the capsule to a path of the slider so that the slider can displace the capsule into the emptying position; and
a cap hinged to the first side of the housing and configured to pivot from an open position into a closed position, the cap in the closed position overlaying the mouthpiece and overlaying the air inlet opening in the manner of a cover;
wherein during the complete aspiration of the contents of the capsule when the cap is in the open position, air and the content of the capsule are inhaled through the mouthpiece sucks in air from the air inlet opening when the air inlet opening is not covered up.

2. The device according to claim 1, wherein the insertion channel is located radially opposite from the air inlet opening and can likewise be overlaid by the cap.

* * * * *

UNITED STATES PATENT AND TRADEMARK OFFICE
CERTIFICATE OF CORRECTION

PATENT NO. : 9,579,473 B2  Page 1 of 1
APPLICATION NO. : 14/114986
DATED : February 28, 2017
INVENTOR(S) : Von Schuckmann It is certified that error appears in the above-identified patent and that said Letters Patent is hereby corrected as shown below:

In the Claims

In Column 8, Line 8 (Line 5 of Claim 1) please change "arrange" to correctly read: --arranged--.

In Column 8, Line 57 (Line 55 of Claim 1) please change "content" to correctly read: --contents--.

In Column 8, Line 58 (Line 56 of Claim 1) after "mouthpiece" please insert: --and a pressure generated via the inhalation through the mouthpiece--.

Signed and Sealed this
Fifth Day of December, 2017

Joseph Matal
*Performing the Functions and Duties of the
Under Secretary of Commerce for Intellectual Property and
Director of the United States Patent and Trademark Office*